(12) United States Patent
Steel (10) Patent No.: US 12,109,885 B2
(45) Date of Patent: Oct. 8, 2024

(54) DRIVER INTOXICATION TEST SYSTEM AND METHOD

(71) Applicant: Gentex Corporation, Zeeland, MI (US)

(72) Inventor: Robert Steel, Coventry (GB)

(73) Assignee: GENTEX CORPORATION, Zeeland, MI (US)

( * ) Notice: Subject to any disclaimer, the term of this patent is extended or adjusted under 35 U.S.C. 154(b) by 0 days.

(21) Appl. No.: 18/181,222

(22) Filed: Mar. 9, 2023

(65) Prior Publication Data
US 2023/0286379 A1    Sep. 14, 2023

Related U.S. Application Data (60) Provisional application No. 63/318,027, filed on Mar. 9, 2022.

(51) Int. Cl.
*A61B 5/00*         (2006.01)
*B60K 28/00*        (2006.01)
(Continued)

(52) U.S. Cl.
CPC .......... B60K 28/063 (2013.01); *A61B 5/4845* (2013.01); *G01N 33/497* (2013.01);
(Continued)

(58) Field of Classification Search
CPC .......... A61B 5/082; A61B 5/16; A61B 5/163; A61B 5/18; A61B 5/4845; A61B 5/6893; A61B 2503/22; B60K 28/02; B60K 28/06; B60K 28/063; B60K 2028/003; G01N 33/497; G01N 33/4972; G06V 20/597; G06V 40/19; G10L 25/51; G10L 25/66
See application file for complete search history.

(56) References Cited

U.S. PATENT DOCUMENTS 6,572,233 B1   6/2003  Northman et al.
8,237,909 B2   8/2012  Ostreko et al.
(Continued)

FOREIGN PATENT DOCUMENTS

JP    2009248891 A     10/2009
JP    2016202975 A  *  12/2016  .......... A61B 5/0075
(Continued)

*Primary Examiner* — Jason D Shanske
*Assistant Examiner* — Daniel M. Keck
(74) *Attorney, Agent, or Firm* — Price Heneveld LLP; Brian James Brewer (57) ABSTRACT

A driver intoxication test system is provided for a vehicle including: a quick intoxication pre-test subsystem for quickly determining whether there is reason to suspect the driver may be intoxicated; an intoxication validation test subsystem for determining whether the driver is intoxicated; and a controller is configured to determine whether the quick intoxication pre-test subsystem has detected a reason to suspect the driver may be intoxicated. When a reason to suspect the driver may be intoxicated has been detected, an intoxication validation test is conducted and it is determined whether the driver has passed the intoxication validation test. When a reason to suspect the driver may be intoxicated has not been detected, the controller does not instruct the intoxication validation test subsystem to conduct an intoxication validation test.

20 Claims, 6 Drawing Sheets

(51) Int. Cl.
  *B60K 28/06* (2006.01)
  *G01N 33/497* (2006.01)
  *G06V 20/59* (2022.01)
  *G06V 40/19* (2022.01)
  *G10L 25/51* (2013.01)

(52) U.S. Cl.
  CPC ............ *G06V 20/597* (2022.01); *G06V 40/19* (2022.01); *G10L 25/51* (2013.01); *A61B 2503/22* (2013.01); *B60K 2028/003* (2013.01)

(56) References Cited

U.S. PATENT DOCUMENTS

| | | |
|---|---|---|
| 8,339,526 B2 | 12/2012 | Minikey, Jr. et al. |
| 8,411,245 B2 | 4/2013 | Lee et al. |
| 10,352,762 B2 | 7/2019 | Carmon |
| 10,997,739 B2 | 5/2021 | Zuta et al. |
| 11,182,915 B2 | 11/2021 | Zuta et al. |
| 11,310,466 B2 | 4/2022 | Amiram et al. |
| 11,465,635 B2 | 10/2022 | Glazman et al. |
| 2002/0186701 A1 | 12/2002 | Kaplan et al. |
| 2009/0169068 A1 | 7/2009 | Okamoto |
| 2012/0078473 A1* | 3/2012 | Ridder ................ A61B 5/1455 701/45 |
| 2013/0238199 A1 | 9/2013 | Williams et al. |
| 2014/0375462 A1* | 12/2014 | Biondo ................ A61B 5/6893 340/576 |
| 2019/0389485 A1 | 12/2019 | Collins, II |
| 2020/0198436 A1 | 6/2020 | Remijn et al. |
| 2020/0353868 A1 | 11/2020 | Schut |
| 2021/0341620 A1 | 11/2021 | Raz et al. |

FOREIGN PATENT DOCUMENTS

| | | |
|---|---|---|
| KR | 1999-0058415 A | 7/1999 |
| KR | 10-2021-0025158 A | 3/2021 |
| KR | 20220020882 A * | 2/2022 |

* cited by examiner

DRIVER INTOXICATION TEST SYSTEM AND METHOD

CROSS-REFERENCE TO RELATED APPLICATION

This application claims priority to and the benefit under 35 U.S.C. § 119(e) of U.S. Provisional Patent Application No. 63/318,027, filed on Mar. 9, 2022, entitled "DRIVER INTOXICATION TEST SYSTEM AND METHOD," by Robert Steel, the entire disclosure of which is incorporated herein by reference.

TECHNOLOGICAL FIELD

The present invention generally relates to a system and method of a vehicle and, more particularly, to a system and method for testing for driver intoxication.

SUMMARY OF THE INVENTION

In one aspect of the invention, a driver intoxication test system is provided for a vehicle. The system includes: a sensor assembly configured for mounting in the vehicle to detect at least one intoxicating substance within the vehicle; an intoxication validation test subsystem configured for mounting in the vehicle, the intoxication validation test subsystem configured to determine whether the driver is intoxicated; and a controller in communication with the sensor assembly and the intoxication validation test subsystem. The controller is configured to: determine whether the sensor assembly has detected an intoxicating substance; when the sensor assembly has detected an intoxicating substance, the controller instructs the intoxication validation test subsystem to conduct an intoxication validation test and determines if the driver has passed the intoxication validation test; and when the sensor assembly has not detected an intoxicating substance, the controller does not instruct the intoxication validation test subsystem to conduct an intoxication validation test.

In another aspect of the invention, a driver intoxication test system is provided for a vehicle. The system includes: a quick intoxication pre-test subsystem for quickly determining whether there is reason to suspect the driver may be intoxicated; an intoxication validation test subsystem configured for mounting in the vehicle, the intoxication validation test subsystem configured to determine whether the driver is intoxicated; and a controller in communication with the quick intoxication pre-test subsystem and the intoxication validation test subsystem. The controller is configured to: determine whether the quick intoxication pre-test subsystem has detected a reason to suspect the driver may be intoxicated; when the quick intoxication pre-test subsystem has detected a reason to suspect the driver may be intoxicated, the controller instructs the intoxication validation test subsystem to conduct an intoxication validation test and determines if the driver has passed the intoxication validation test; and when the quick intoxication pre-test subsystem has not detected a reason to suspect the driver may be intoxicated, the controller does not instruct the intoxication validation test subsystem to conduct an intoxication validation test.

In another aspect of the invention, a method is provided for testing whether a driver is intoxicated within a vehicle having a vehicle ignition lock-out, the method comprising: performing a quick intoxication pre-test using a sensor subassembly for quickly determining whether there is reason to suspect the driver may be intoxicated; when the quick intoxication pre-test has detected a reason to suspect the driver may be intoxicated, performing an intoxication validation test to determine if the driver is intoxicated; when the intoxication validation test determines that the driver is intoxicated, sending a signal to the vehicle ignition lock-out to prevent the vehicle from starting; when the intoxication validation test determines that the driver is not intoxicated, sending a signal to the vehicle ignition lock-out to allow the vehicle to be started; and when the quick intoxication pre-test has not detected a reason to suspect the driver may be intoxicated, sending a signal to the vehicle ignition lock-out to allow the vehicle to be started without conducting the intoxication validation test.

These and other features, advantages, and objects of the present device will be further understood and appreciated by those skilled in the art upon studying the following specification, claims, and appended drawings.

BRIEF DESCRIPTION OF THE DRAWINGS

The embodiments will now be described with reference to the following drawings, in which.

DETAILED DESCRIPTION OF EMBODIMENTS

For purposes of description herein, it will be understood that the specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone;

A and B in combination; A and C in combination; B and C in combination; or A, B, and C in combination.

The embodiments below relate to a system and method for implementing a driver intoxication test to determine if the driver is in a condition suitable for driving a vehicle. As part of the recently-passed infrastructure bill, anti-drunk driving technology must be built into new cars. However, current impairment tests take time and will be challenging for automakers to implement. People want to get in and start their vehicle right away. Some driver intoxication tests can take 30 seconds to several minutes or more.

Figure 1:
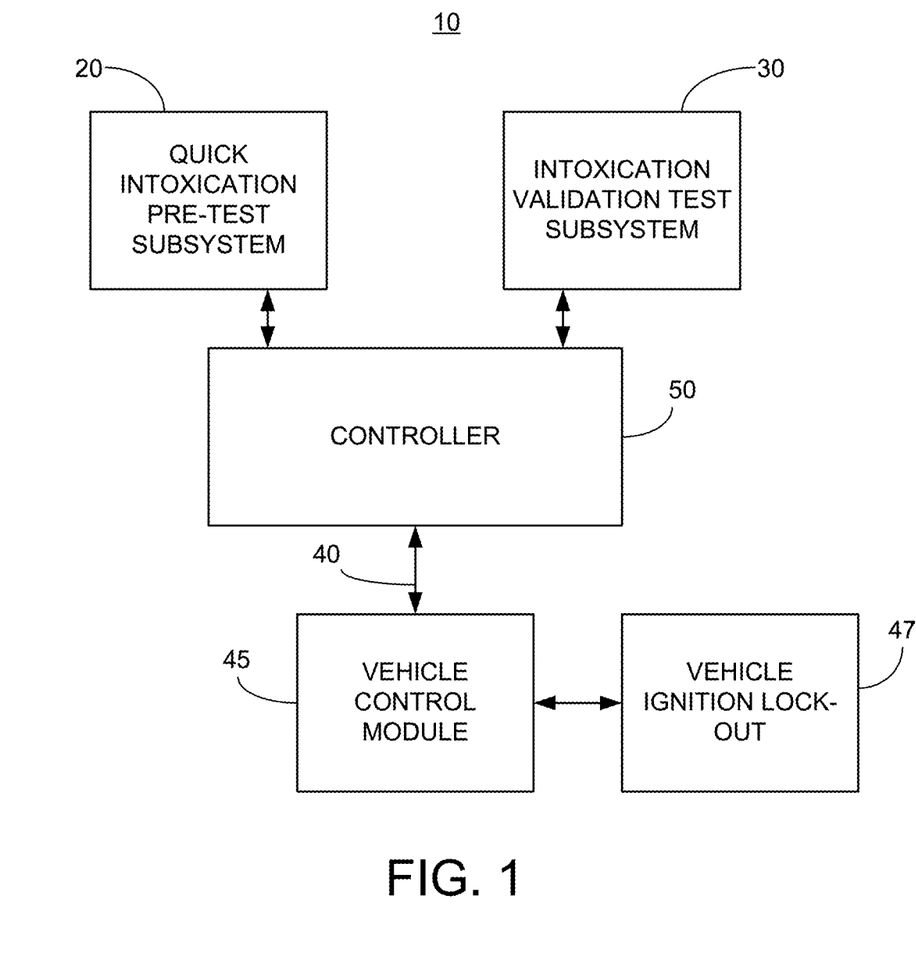
FIG. 1 is a block diagram of a system for testing driver intoxication for a vehicle.

FIG. 1 shows an example of a driver intoxication test system 10 for a vehicle. The system 10 may include: a quick intoxication pre-test subsystem 20 for quickly determining whether there is reason to suspect the driver may be intoxicated; an intoxication validation test subsystem 30 configured for mounting in the vehicle, the intoxication validation test subsystem 30 configured to determine whether the driver is intoxicated; and a controller 50 in communication with the quick intoxication pre-test subsystem 20 and the intoxication validation test subsystem 30. The controller 50 is configured to: determine whether the quick intoxication pre-test subsystem 20 has detected a reason to suspect the driver may be intoxicated; when the quick intoxication pre-test subsystem 20 has detected a reason to suspect the driver may be intoxicated, the controller 50 instructs the intoxication validation test subsystem 30 to conduct an intoxication validation test and determines if the driver has passed the intoxication validation test; and, when the quick intoxication pre-test subsystem 20 has not detected a reason to suspect the driver may be intoxicated, the controller 50 does not instruct the intoxication validation test subsystem 30 to conduct an intoxication validation test.

The controller 50 may be coupled to a vehicle bus 40 that, in turn, may be coupled to a vehicle control module 45. The vehicle bus 40 may be a CAN bus, a LIN bus, or an Ethernet bus. The controller 50 may also be coupled to the vehicle control module 45 by wireless communication, a dedicated wired connection, or any other form of connection. The vehicle control module 45 may be coupled to a vehicle ignition lock-out 47 so as to enable or disable the vehicle's ignition. In this manner, the controller 50 may send a signal to the vehicle control module 45 that enables or disables the vehicle ignition based on whether the driver has passed the intoxication validation test. In the present application, the controller 50 is thus further configured to transmit a signal to enable the vehicle ignition when the quick intoxication pre-test subsystem 20 has not detected a reason to suspect the driver may be intoxicated or the controller 50 determines the driver has passed the intoxication validation test.

By first performing a quick intoxication test, the system 10 may determine within a matter of seconds, whether there is a reason to suspect the driver may be intoxicated before initiating a more lengthy and accurate intoxication validation test. Thus, drivers that do not provide any reason for suspicion will not be required to proceed through a more lengthy test each time they enter the vehicle.

Figure 2:
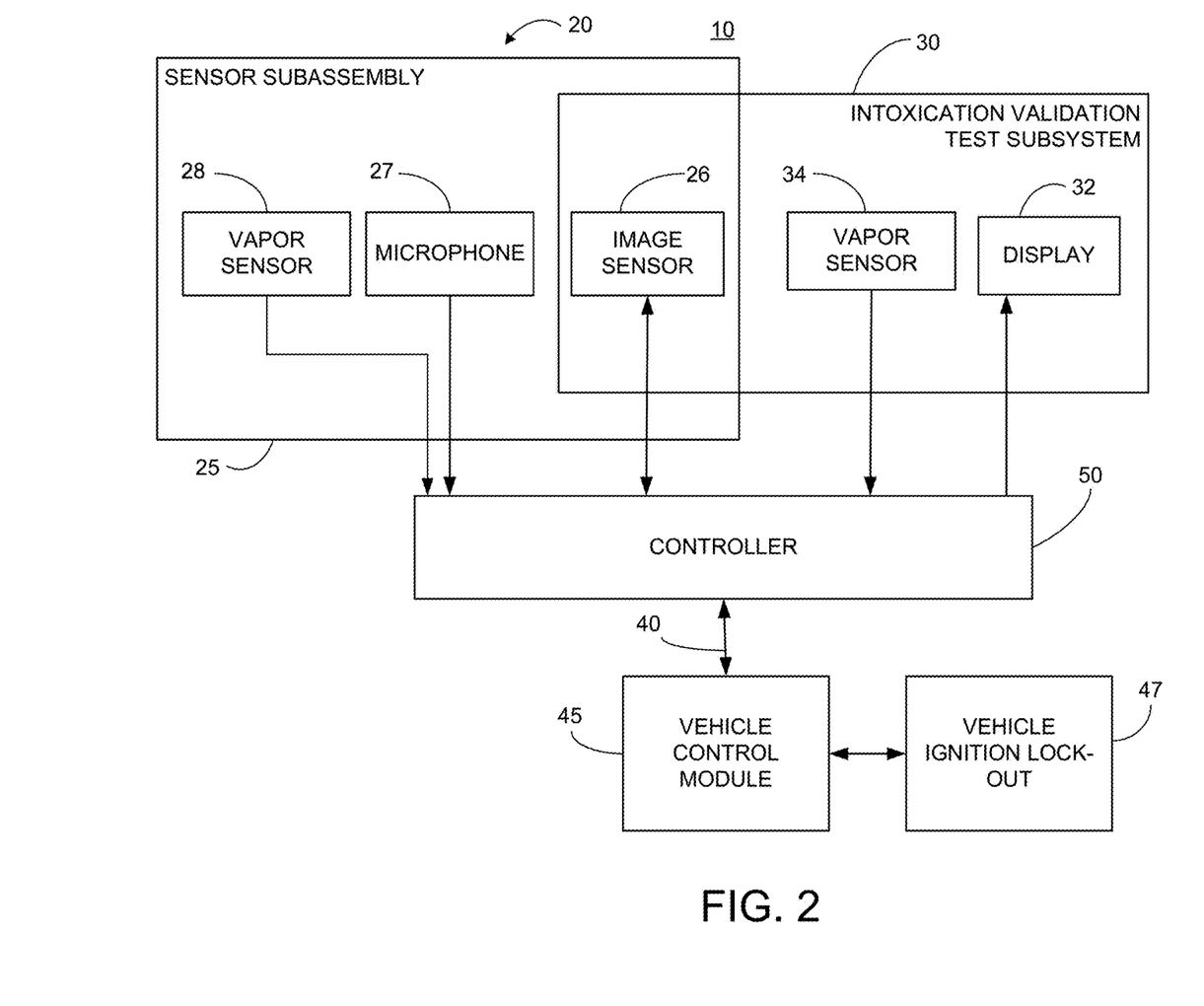
FIG. 2 is a block diagram of the system for testing driver intoxication shown in FIG. 1.

As shown in FIG. 2, the quick intoxication pre-test subsystem 20 may include a sensor subassembly 25 configured to detect at least one intoxicating substance within the vehicle. The sensor subassembly 25 may be mounted in a rearview assembly.

The sensor subassembly 25 may include an image sensor 26 for capturing images of an interior of the vehicle to visually detect the presence of intoxicating substances or to detect driver movements that provide a reason to suspect the driver is intoxicated. The controller 50 may utilize artificial intelligence to analyze the images for suspicious behavior.

The sensor subassembly 25 may additionally or alternatively include a microphone 27 for capturing the driver's voice to detect whether the driver may be intoxicated. For example, the driver may be prompted to speak upon entering the vehicle. The microphone 27 may then pick up such speech and the controller 50 may process the speech to detect any slurring or other factors that may give a reason to suspect that the driver may be intoxicated.

The quick intoxication pre-test subsystem 20 may additionally or alternatively include a vapor sensor 28 for sensing vapors of intoxicating substances within the vehicle. Such a vapor sensor 28 may be of the type that has a plurality of nanofiber chemical sensors, wherein at least a plurality of nanofibers in at least one of the nanofiber chemical sensors have been synthesized with specific functional groups to allow the nanofiber chemical sensors to detect particular materials, such as various drugs. The controller 50 may be configured for analyzing signals from the nanofiber chemical sensors and detecting at least one particular material based on the signals from the nanofiber chemical sensors.

The intoxication validation test subsystem 30 may include a display 32 and an image sensor 26 for capturing images of eyes of the driver of the vehicle. The controller 50 analyzes the images to determine the driver's aptitude for driving the vehicle and thereby to determine if the driver has passed an intoxication validation test. An example of such a subsystem is disclosed below with reference to FIGS. 4-6B.

The intoxication validation test subsystem 30 may additionally or alternatively include a vapor sensor 34 for capturing vapors blown from the driver in the direction of the vapor sensor 34. The controller 50 analyzes an output from the vapor sensor 34 to determine if the driver has passed an intoxication validation test. The vapor sensor 34 may be separate from vapor sensor 28 or may be the same sensor.

The controller 50 may be integrated in the image sensor 26 or may be physically separate from the image sensor 26.

The controller 50 may include one or more processors configured to selectively perform the tasks described above, among other things. Thus, it will be appreciated that embodiments of the invention described herein may be comprised of one or more conventional processors and unique stored program instructions that control one or more processors to implement, in conjunction with certain non-processor circuits, some, most, or all of the functions of the present system and/or an interior rearview assembly. The non-processor circuits may include, but are not limited to, signal drivers, clock circuits, power source circuits, and/or user input devices. As such, these functions may be interpreted as steps of a method used in utilizing or constructing a classification system. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, the methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

Figure 3:
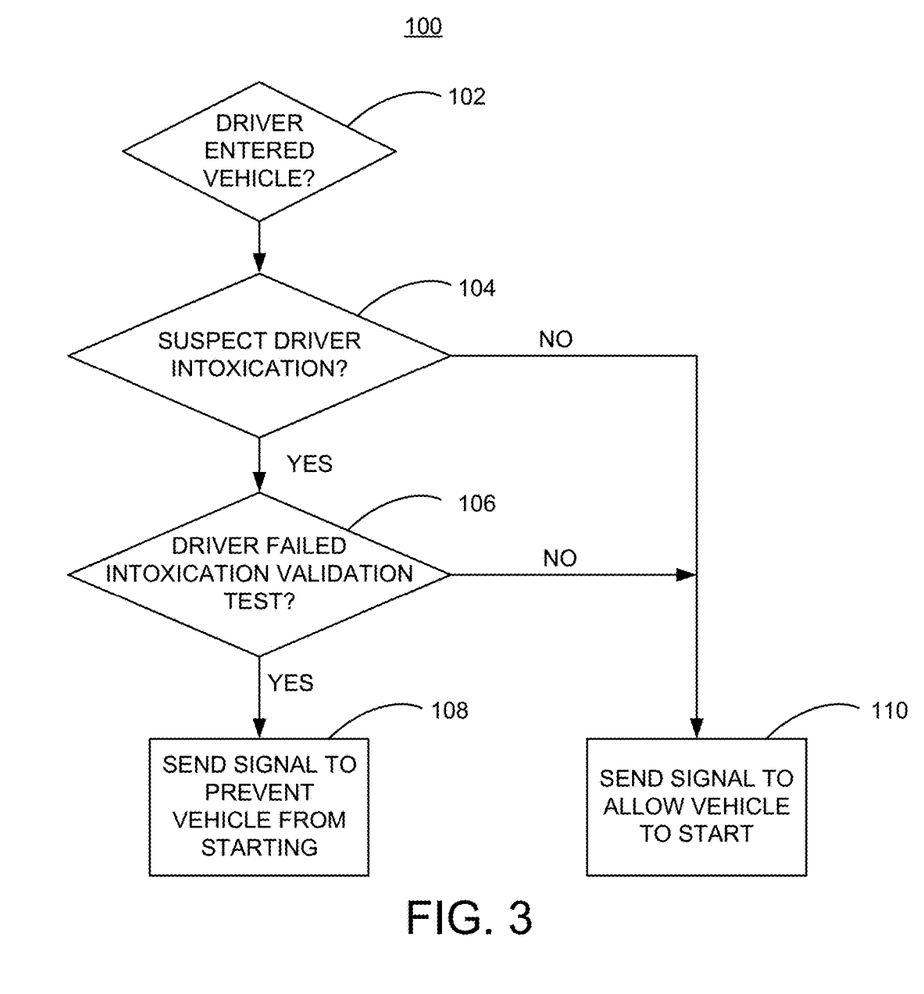
FIG. 3 is a flowchart illustrating a method for testing driver intoxication.

Having described a driver intoxication test system above, a method 100 for testing driver intoxication is now described with reference to FIG. 3. This method may be implemented through the execution of a computer algorithm by the controller 50.

The method 100 for testing whether a driver is intoxicated within a vehicle having a vehicle ignition lock-out 47, will typically be initiated when it is determined in step 102 that a driver has entered the vehicle. The method 100 begins with performing a quick intoxication pre-test using a sensor subassembly for quickly determining whether there is reason to suspect the driver may be intoxicated (step 104). If the quick intoxication pre-test has detected a reason to suspect the driver may be intoxicated, the method 100 includes performing an intoxication validation test to determine if the driver is intoxicated (step 106). If the intoxication validation test determines that the driver is intoxicated, a signal is sent to the vehicle ignition lock-out 47 to prevent the vehicle from starting (step 108). If the intoxication validation test determines that the driver is not intoxicated, a signal is sent to the vehicle ignition lock-out 47 to allow the vehicle to be started (step 110). If the quick intoxication pre-test has not detected a reason to suspect the driver may be intoxicated (step 104), signal is sent to the vehicle ignition lock-out to allow the vehicle to be started without conducting the intoxication validation test (step 110).

Figure 4:
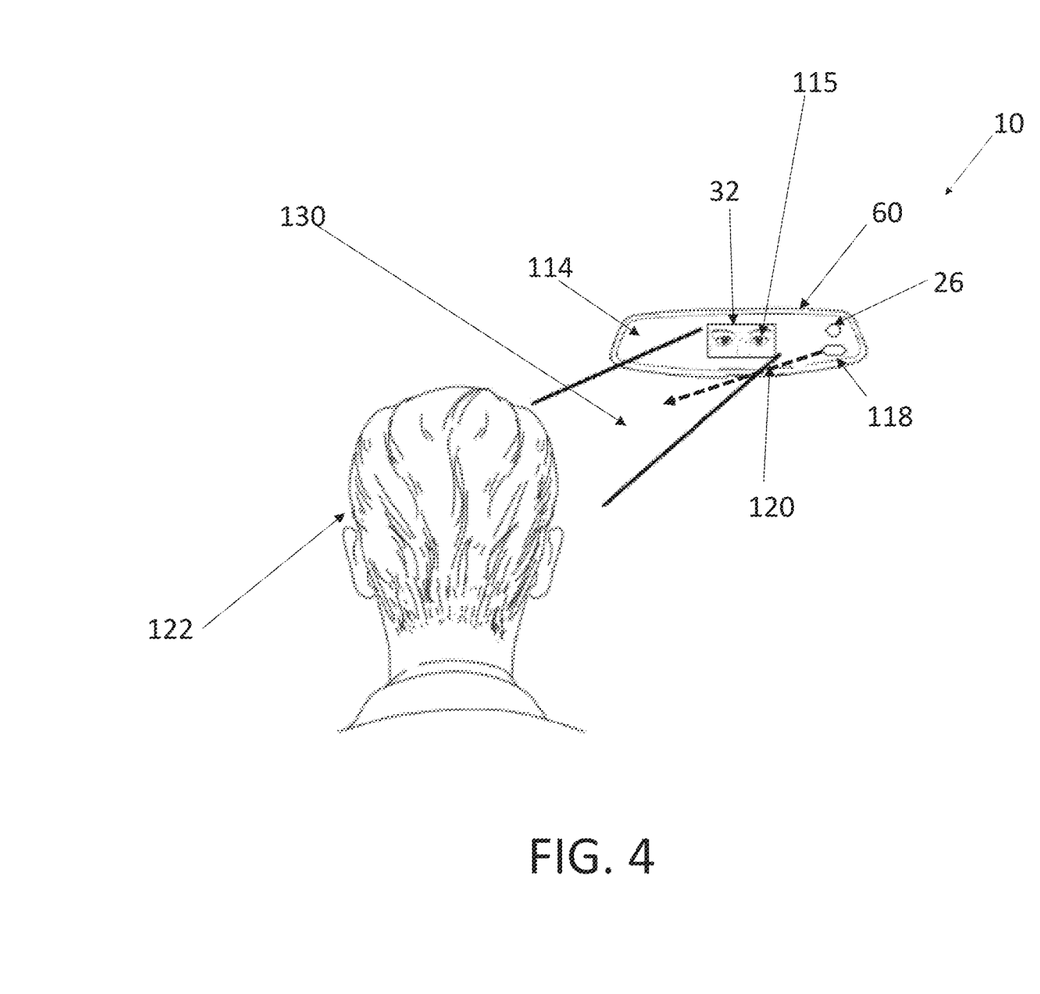
FIG. 4 is a perspective view of a driving aptitude test system incorporated in an interior rearview assembly.

FIG. 4 shows an example of an intoxication validation test subsystem 30 for a vehicle that uses a display 32 and an image sensor 26 and is mounted in the vehicle. This particular example, shows the display 32 and the image sensor 26 are mounted in an interior rearview assembly 60 of the vehicle. It will be appreciated, however, that the display 32 and the image sensor 26 may be mounted elsewhere in the vehicle.

The rearview assembly 60 may have the display 32 extending across substantially the full length and height of the viewing area of the rearview assembly 60 or the display 32 may extend across a portion thereof.

The image sensor 26 may be mounted anywhere proximate the display 32 and is shown in FIG. 4 as mounted behind a front substrate 114 of the rearview assembly 60. The image sensor 26 may also be mounted in the rearview assembly 60 adjacent to the display 32. The image sensor 26 is mounted to have a field of view 130 that includes an interior space where the head of a driver 122 is expected to be located. By mounting the display 32 and the image sensor 26 in the vehicle, fixed conditions (lighting, distance, background) can be achieved unlike prior systems incorporated into cell phones. The image sensor 26 can be configured to sense radiation in the NIR spectral range.

The intoxication validation test subsystem 30 may further include at least one light source 118 configured to output an emission 120 of light towards the head of the driver 122. The light source 118 may correspond to one or more infrared emitters configured to output light in the near infrared (NIR) range to illuminate the driver 122 in low light conditions. The light source 118 may be mounted in the rearview assembly 60 or elsewhere in the vehicle.

As explained further below, the display 32 may initially display a preview window 126 showing the driver's eyes 115 so that the driver 122 may be sure that their head is positioned correctly to conduct the intoxication validation test.

Referring back to FIG. 2, the controller 50 may be configured to: control the display 32 to cause a moving marker 150 (FIG. 5) or one or more patterns to be displayed; process images captured of the eyes 115 of the driver 122 while the moving marker 150 or one or more patterns is displayed; and analyze the images to determine the driver's aptitude for driving the vehicle and thereby to determine if the driver 22 has passed the intoxication validation test. The controller 50 may be located anywhere in the vehicle and specifically may be located in the rearview mirror assembly 60.

Another advantage of the present embodiments is that the driver intoxication test system 10 may be implemented using the display 32 and image sensor 26 already used in the vehicle for a driver identification (DID) system. This would eliminate the need to provide a dedicated image sensor to implement a driver intoxication test. Furthermore, features of the DID system may be used to ensure that the person taking the driver intoxication test is, in fact, the same person that remains in the driver's seat and starts the vehicle. In other words, the system 10 may authenticate the identity of the driver 122 using biometrics or the like, administer the driver intoxication test to the driver 122, and monitor the imaged scene to detect whether the driver 122 who passed the test remains in the driver's seat or if the driver 122 leaves and then another person sits in the driver's seat who did not take the intoxication test. Examples of DID systems are disclosed in commonly-owned U.S. Patent Publication Nos. 2019/0389485 A1, 2020/0353868 A1, and 2002/0186701 A1, the entire disclosures of which are incorporated herein by reference.

The display 32, the image sensor 26, and the controller 50 of the driver intoxication test system 10 may also be used as a driver monitoring system (DMS) for detecting whether the driver 122 appears drowsy or falls asleep while driving the vehicle. The DMS may also monitor for inattentiveness and other driver states. In addition, the DMS may monitor for the presence/absence of a driver. If the DMS detects that the driver is no longer present, the system may reset the aptitude verification. Examples of DMSs are disclosed in commonly-owned U.S. Patent Publication No. 2002/0186701 A1, the entire disclosure of which is incorporated herein by reference.

Driver intoxication may be assessed based on ocular measurement as a response to a stimulus. In such a setup, the image sensor 26 captures images of the driver's eyes 115 and together with the controller 50, monitors the driver's ocular response. The response may include any one or more of: eye motion and target tracking accuracy, pupil dilation, saccadic eye motion, and eyelid motion (closure) frequency, rate, and velocity.

In a sub-category, the ocular parameters are measured in response to a controlled stimulus, which can be presented on the display 32. In such a setup, the controller 50 controls the display 32 to show moving markers 150 (FIG. 5) such as a cross mark, and the driver 122 is instructed to follow the marker 150 with their eyes 115 only. By using the image sensor 26, the system tracks the driver's eye activity and assesses the accuracy of gaze tracking, which accuracy infers the intoxication score.

Figure 6A:
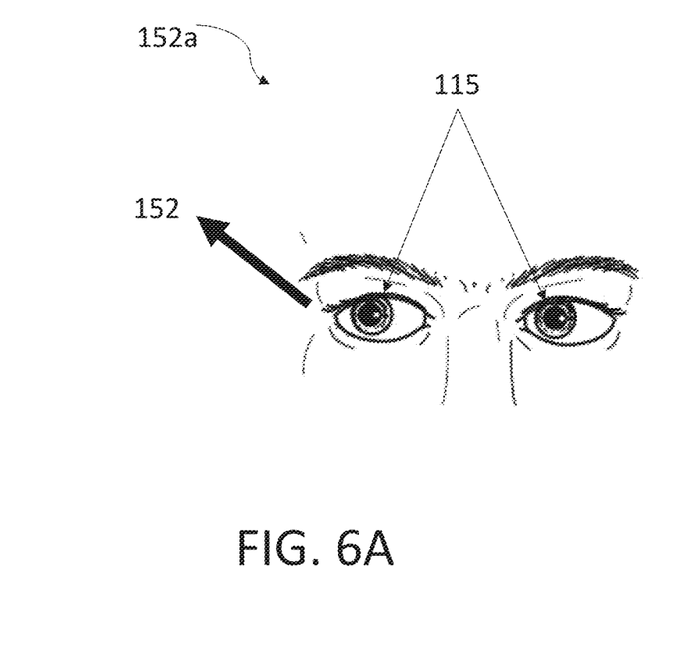
FIG. 6A is a detailed view of exemplary image data demonstrating a gaze direction to the side and upward direction.
Figure 6B:
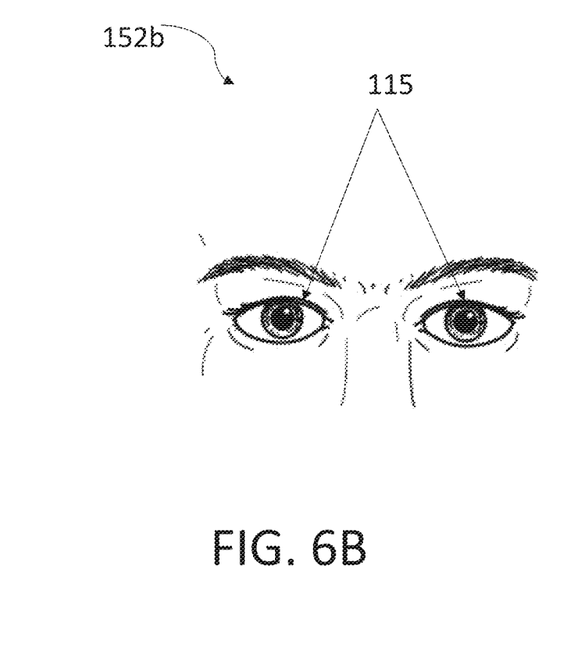
FIG. 6B is a detailed view of exemplary image data demonstrating a gaze direction in the forward direction.

Referring to FIGS. 6A and 6B, first image data 152a and second image data 152b are shown. In some implementations, the controller 50 may be configured to monitor an eye position and/or a gaze direction of the eyes 115 of the driver 122. As depicted in FIG. 6A, the first image data 152a demonstrates the eyes 115 pitched in a gaze direction 152 in a side and upward direction 152 indicated by an arrow. In contrast, FIG. 6B depicts the second image data 152b demonstrating the eyes 115 focused in a gaze direction directed generally forward. In relation to the operation of the driver intoxication test system 10, the gaze direction 152 may correspond to the eyes 115 of the driver 122 aligned with or directed toward a portion of the display 32, which may depict a moving target 150. Accordingly, the controller 50 may process the image data to determine the gaze direction 152 of the driver 122 relative to the display 32. Gaze direction can be estimated from the images of the eyes in several ways. First, the image sensor may monitor the intensity of back-reflection of the illumination from the retina. The reflection intensity changes with eye angle, hence affecting the observed pupil brightness (similar to redeye effect that sometime occurs when photographing with flash). Second, the system may measure the offset between the pupil and the glint point, which is the reflection of the illuminator off the cornea. Third, the system may measure the offset of the pupil from the observed estimated center of the eyeball.

Figure 5:
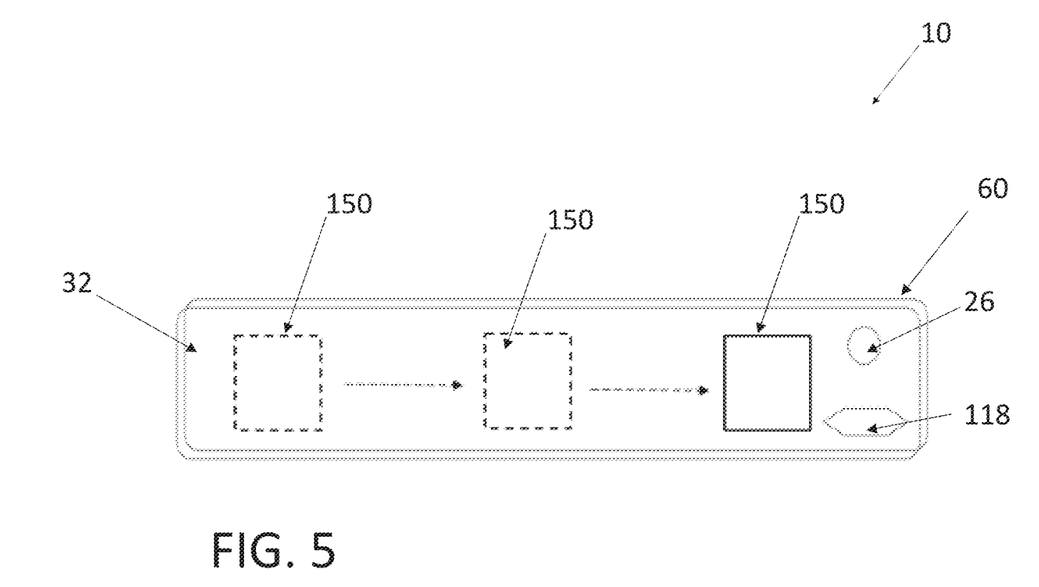
FIG. 5 is a detailed view of a display of the driving aptitude test system of FIGS. 1 and 2 comprising a moving target icon.

As noted above, the display 32 may show a moving marker 150 and/or one or more patterns. With the moving marker 150, the delay in movement of the eyes 115 while tracking the moving marker 150 may be monitored. With one or more patterns, pupil contraction can be measured in response to bright light flickering. This means the projected images are fixed or alternating patterns.

To prevent drivers from switching after being tested, the system 10 may track the driver's head while in the vehicle, either independently or as part of the operation of DMS. Whenever the vehicle is stopped and the driver's head is lost from the field of view of the image sensor 26 for more than a certain period, the system 10 may be configured to require a new intoxication test. Alternatively, if the intoxication test system 10 is combined with a DID system, the system 10 may be configured to require a driver intoxication test when it detects change in driver identity after stopping of the vehicle. On the other hand, if the system 10 detects that the driver that just entered the vehicle is the same one that had exited a first time period (e.g., two minutes) ago, and was validated at the beginning of the drive a second time period (e.g., 20 minutes) ago, the system 10 may accept the driver as validated and not demand a new test.

Another way the driver intoxication test system 10 may determine that the driver has changed after the intoxication test has been taken is whether an existing seat occupancy detector used to sound a seat belt warning or to activate an airbag, indicates the driver is no longer seated in the driver's seat for a period of time following first detection. Another way is to sense whether the driver's door is open in which case, a retest may be required. Further, any sensor that can detect a person, like a motion detection system, can be used to look for large changes that may indicate that the driver has changed.

Preventing driver switch may also be a useful feature for trucks in long haul fleets. For example, problems exist where a professional driver would switch and "sell" their driving task to a non-authorized substitute driver, therefore creating insurance and liability issues for the company.

Various intoxication validation tests may be conducted using the structure of system 30 described above. A method of conducting an intoxication validation test may be implemented by the controller 50. In the method, using the display 32 as a reference, the driver 122 may adjust the position of the interior rearview assembly 60 such that the image appearing on the display 32 is properly aimed and focused on the eyes 115. Next, the driver 122 is instructed by an audible voice prompt and/or text message displayed on display 32 to follow the moving marker 150 displayed on display 32. The controller 50 will then display the moving marker 150, which may move in a selected pattern. Such a pattern of movement may be horizontal and/or vertical or in a circle or along a sine wave, for example. The speed of movement may also be altered. At the same time, the controller 50 receives image data from the image sensor 26 and determines any delay in movement of the driver's eyes 115 relative to the movement of the marker 150. The greater the delay in movement of the driver's gaze, the lower the intoxication score. The controller 50 may then use a look up table or formula to determine a level of intoxication as a function of the delay. The controller 50 may optionally perform other tests or additional tests that may determine target tracking accuracy, pupil dilation, saccadic eye motion, and eyelid motion (closure) frequency, rate, and velocity. The controller 50 may factor in all of these tests to determine a single intoxication score, or if any one test is failed, a failing score may be given.

The driver intoxication test system 10 described above provides several advantages over prior art systems. Specifically, these advantages include: (1) allowing the driver intoxication test system 10 to be built into a vehicle; (2) utilizing an existing driver monitoring camera and existing vehicle displays; (3) integrating at least a portion of the system into a rearview assembly 60 equipped with both an image sensor 26 and a display 32; (4) naturally preventing switching of drivers after taking the intoxication test; and (5) allowing the intoxication test to be taken at a more controlled environment (subject, pose, distance, illumination) to thereby improve testing accuracy.

Although demonstrated as incorporated in the rearview assembly 60, it may be understood that one or more components of the driver intoxication test system 10 may be incorporated in other portions of the vehicle (e.g. infotainment display, panels, an overhead console, visor, center consoles, a steering wheel, etc.).

Additionally, in some embodiments, the light source 118 may be positioned separate from the rearview assembly 60 (e.g., in an overhead console, vehicle pillar, etc.), while still providing illumination in a field of view of the driver intoxication test system 10.

The display 32 may be configured as an LCD, LED, OLED, plasma, DLP, or other display type. Examples of displays that may be utilized are disclosed in U.S. Pat. No. 6,572,233, entitled "Rearview Display Mirror," U.S. Pat. No. 8,237,909, entitled "Vehicular Rearview Mirror Assembly including Integrated Backlighting for a Liquid Crystal Display (LCD)," U.S. Pat. No. 8,411,245, entitled "Multi-Display Mirror System and Method for Expanded View around a Vehicle," and U.S. Pat. No. 8,339,526, entitled "Vehicle Rearview Mirror Assembly Including a High Intensity Display," all of which are incorporated herein by reference in their entirety.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed is:

1. A driver intoxication test system for a vehicle, the system comprising:
   a sensor assembly configured for mounting in the vehicle to detect at least one intoxicating substance within the vehicle;
   an intoxication validation test subsystem configured for mounting in the vehicle, the intoxication validation test subsystem configured to determine whether the driver is intoxicated; and
   a controller in communication with the sensor assembly and the intoxication validation test subsystem, the controller configured to:
   determine whether the sensor assembly has detected an intoxicating substance;
   when the sensor assembly has detected an intoxicating substance, the controller instructs the intoxication validation test subsystem to conduct an intoxication validation test and determines if the driver has passed the intoxication validation test; and
   when the sensor assembly has not detected an intoxicating substance, the controller does not instruct the intoxication validation test subsystem to conduct an intoxication validation test.

2. The system according to claim 1, wherein the controller is further configured to transmit a signal to enable vehicle ignition when the sensor assembly has not detected an intoxicating substance or when the controller determines the driver has passed the intoxication validation test.

3. The system according to claim 1, wherein the sensor assembly is mounted in a rearview assembly.

4. The system according to claim 1, wherein the sensor assembly comprises an image sensor for capturing images of an interior of the vehicle to visually detect the presence of intoxicating substances.

5. The system according to claim 1, wherein the sensor assembly comprises a microphone for capturing the driver's voice to detect whether the driver may be intoxicated.

6. The system according to claim 1, wherein the sensor assembly comprises a vapor sensor for sensing vapors of intoxicating substances within the vehicle.

7. The system according to claim 1, wherein the intoxication validation test subsystem comprises a display and an image sensor for capturing images of eyes of a driver of the vehicle, wherein the controller analyzes the images to determine the driver's aptitude for driving the vehicle and thereby to determine if the driver has passed an intoxication validation test.

8. The system according to claim 7, wherein the controller is integrated in the image sensor.

9. The system according to claim 7, wherein the controller is physically separate from the image sensor.

10. The system according to claim 1, wherein the intoxication validation test subsystem comprises a vapor sensor for capturing vapors blown from the driver in the direction of the vapor sensor, wherein the controller analyzes an output from the vapor sensor to determine if the driver has passed an intoxication validation test.

11. A driver intoxication test system for a vehicle, the system comprising:
    a quick intoxication pre-test subsystem for quickly determining whether there is reason to suspect the driver may be intoxicated;
    an intoxication validation test subsystem configured for mounting in the vehicle, the intoxication validation test subsystem configured to determine whether the driver is intoxicated; and
    a controller in communication with the quick intoxication pre-test subsystem and the intoxication validation test subsystem, the controller configured to:
    determine whether the quick intoxication pre-test subsystem has detected a reason to suspect the driver may be intoxicated;
    when the quick intoxication pre-test subsystem has detected a reason to suspect the driver may be intoxicated, the controller instructs the intoxication validation test subsystem to conduct an intoxication validation test and determines if the driver has passed the intoxication validation test; and when the quick intoxication pre-test subsystem has not detected a reason to suspect the driver may be intoxicated, the controller does not instruct the intoxication validation test subsystem to conduct an intoxication validation test.

12. The system of claim 11, wherein the quick intoxication pre-test subsystem comprises a sensor assembly configured to detect at least one intoxicating substance within the vehicle.

13. The system of claim 12, wherein the sensor assembly is mounted in a rearview assembly.

14. The system of claim 12, wherein the sensor assembly comprises an image sensor for capturing images of an interior of the vehicle to visually detect the presence of intoxicating substances.

15. The system of claim 12, wherein the sensor assembly comprises a microphone for capturing the driver's voice to detect whether the driver may be intoxicated.

16. The system of claim 11, wherein the controller is further configured to transmit a signal to enable vehicle ignition when the quick intoxication pre-test subsystem has not detected a reason to suspect the driver may be intoxicated or the controller determines the driver has passed the intoxication validation test.

17. The system of claim 11, wherein the quick intoxication pre-test subsystem comprises a vapor sensor for sensing vapors of intoxicating substances within the vehicle.

18. The system of claim 11, wherein the intoxication validation test subsystem comprises a display and an image sensor for capturing images of eyes of a driver of the vehicle, wherein the controller analyzes the images to determine the driver's aptitude for driving the vehicle and thereby to determine if the driver has passed an intoxication validation test.

19. The system of claim 11, wherein the intoxication validation test subsystem comprises a vapor sensor for capturing vapors blown from the driver in the direction of the vapor sensor, wherein the controller analyzes an output from the vapor sensor to determine if the driver has passed an intoxication validation test.

20. A method for testing whether a driver is intoxicated within a vehicle having a vehicle ignition lock-out, the method comprising:
   performing a quick intoxication pre-test using a sensor subassembly for quickly determining whether there is reason to suspect the driver may be intoxicated;
   when the quick intoxication pre-test has detected a reason to suspect the driver may be intoxicated, performing an intoxication validation test to determine if the driver is intoxicated;
   when the intoxication validation test determines that the driver is intoxicated, sending a signal to the vehicle ignition lock-out to prevent the vehicle from starting;
   when the intoxication validation test determines that the driver is not intoxicated, sending a signal to the vehicle ignition lock-out to allow the vehicle to be started; and
   when the quick intoxication pre-test has not detected a reason to suspect the driver may be intoxicated, sending a signal to the vehicle ignition lock-out to allow the vehicle to be started without conducting the intoxication validation test.

* * * * *